US012465490B2

(12) United States Patent
Tallarida et al.

(10) Patent No.: US 12,465,490 B2
(45) **Date of Patent: *Nov. 11, 2025**

(54) SYSTEMS, APPARATUS AND METHODS TO REPAIR OPERATION OF A HEART VALVE

(71) Applicant: PRIMO MEDICAL GROUP, INC., Stoughton, MA (US)

(72) Inventors: Steven J. Tallarida, Mansfield, MA (US); John M. Butziger, East Greenwich, RI (US)

(73) Assignee: PRIMO MEDICAL GROUP, INC., Stoughton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/211,978

(22) Filed: Jun. 20, 2023

(65) Prior Publication Data

US 2024/0164904 A1 May 23, 2024

Related U.S. Application Data

(63) Continuation of application No. 16/949,611, filed on Nov. 6, 2020, now Pat. No. 11,678,985.

(Continued)

(51) Int. Cl.
*A61F 2/24* (2006.01)

(52) U.S. Cl.
CPC .......... *A61F 2/2457* (2013.01); *A61F 2/2427* (2013.01); *A61F 2210/009* (2013.01)

(58) Field of Classification Search
CPC ........ A61F 2250/006; A61F 2250/0039; A61F 2250/0007; A61F 2220/0033;

(Continued)

(56) References Cited

U.S. PATENT DOCUMENTS 4,832,054 A 5/1989 Bark
6,478,783 B1 11/2002 Moorehead (Continued)

FOREIGN PATENT DOCUMENTS

JP S64500166 A 1/1989
JP H02156962 A 6/1990

(Continued)

OTHER PUBLICATIONS

Examination Report from related Application No. 2019224138 mailed Nov. 14, 2023.4 pages.

(Continued)

*Primary Examiner* — Jerrah Edwards

(74) *Attorney, Agent, or Firm* — Grossman, Tucker, Perreault & Pfleger, PLLC

(57) ABSTRACT

An implant configured to control travel of a leaflet of a heart valve, the implant comprising a first implant member, the first implant member having a first implant member first fastener, a first implant member second fastener, a tether connecting the first implant member first fastener and the first implant member second fastener and a first implant member connector slidably disposed on the tether; a second implant member, the second implant member having a second implant member connector and a second implant member anchor; wherein the first implant member connector and the second implant member connector are magnetically couplable, and wherein at least one of the first implant member connector and the second implant member connector comprises a permanent magnet.

8 Claims, 9 Drawing Sheets

Related U.S. Application Data

(60) Provisional application No. 62/932,149, filed on Nov. 7, 2019.

(58) Field of Classification Search
CPC ...... A61F 2220/0025; A61F 2220/0016; A61F 2210/009; A61F 2/2451; A61F 2/2427; A61F 2/2457
See application file for complete search history.

(56) References Cited

U.S. PATENT DOCUMENTS

| | | | | |
|---|---|---|---|---|
| 7,186,236 | B2 | 3/2007 | Gibson et al. | |
| 7,361,190 | B2 | 4/2008 | Shaoulian et al. | |
| 10,105,225 | B2 | 10/2018 | Clague et al. | |
| 10,512,766 | B2 | 12/2019 | Tallarida et al. | |
| 11,678,985 | B2 * | 6/2023 | Tallarida | A61B 17/0401 623/2.11 |
| 2004/0260393 | A1 | 12/2004 | Rahdert et al. | |
| 2006/0015178 | A1 | 1/2006 | Moaddeb et al. | |
| 2007/0027460 | A1 | 2/2007 | Case et al. | |
| 2007/0144539 | A1 * | 6/2007 | van der Burg | A61B 17/0401 606/1 |
| 2008/0195126 | A1 * | 8/2008 | Solem | A61F 2/2457 606/155 |
| 2009/0306686 | A1 | 12/2009 | Ohdaira | |
| 2011/0060407 | A1 * | 3/2011 | Ketai | A61B 17/0644 623/2.37 |
| 2011/0087249 | A1 | 4/2011 | Rodrigues et al. | |
| 2012/0109080 | A1 | 5/2012 | Manesis et al. | |
| 2012/0245678 | A1 * | 9/2012 | Solem | A61M 60/871 623/2.36 |
| 2014/0378942 | A1 | 12/2014 | Christian et al. | |
| 2015/0073547 | A1 * | 3/2015 | Eliasen | A61F 2/2427 623/2.36 |
| 2015/0201973 | A1 * | 7/2015 | Lindemann | A61B 17/7053 606/279 |
| 2015/0289976 | A1 * | 10/2015 | Machold | A61F 2/2442 623/2.37 |
| 2019/0000620 | A1 | 1/2019 | Shaolian et al. | |
| 2019/0262597 | A1 | 8/2019 | Rodgers | |
| 2020/0337840 | A1 * | 10/2020 | Reich | A61F 2/2457 |
| 2021/0015475 | A1 * | 1/2021 | Lau | A61B 17/0401 |

FOREIGN PATENT DOCUMENTS

| | | | |
|---|---|---|---|
| WO | 8704631 | A1 | 8/1987 |
| WO | 2016054387 | A1 | 4/2016 |

OTHER PUBLICATIONS

Extended European Search Report from related Application No. 20885506.4 mailed Nov. 13, 2023.

Office Action from related Japanese Appln. No. 2020-544829, dated Sep. 21, 2023. English translation attached. 5 pages.

Office Action from related Canadian Appln. No. 3,030,172, dated Sep. 21, 2023. 4 pages.

Office Action from related European Appln. No. 17824871.2 dated Nov. 11, 2023. 4 pages.

International Search Report and Written Opinion mailed Feb. 3, 2021, issued in PCT Patent Application No. PCT/US2020/070754, 9 pages.

Office Action from related Japanese Appln. No. 2020-544829, dated Dec. 14, 2022. English translation attached.

* cited by examiner

SYSTEMS, APPARATUS AND METHODS TO REPAIR OPERATION OF A HEART VALVE

This application is a continuation of U.S. patent application Ser. No. 16/949,611 filed 6 Nov. 2020, now U.S. Pat. No. 11,678,985, and claims the benefit of 62/932,149, filed 7 Nov. 2019, the teachings both of which are hereby incorporated by reference in their entirety.

FIELD

The present disclosure relates to systems, apparatus and methods to repair operation of a heart valve, and more particularly repair the chordae tendineae of a human heart.

BACKGROUND

Myxomatous degeneration, mitral valve prolapse, bacterial endocarditis, and rheumatic heart disease are all examples of causes of chordae tendineae damage. When damaged or ruptured, the associated valve leaflet's function can become compromised, potentially allowing for regurgitation from ventricle to atrium. Surgical techniques exist in which chordae tendineae are replaced with PTFE sutures, but many of these techniques require atriotomy, and even those using a transcatheter approach are complicated by suture length adjustment and anchoring procedures. Proper suture length is critical for proper leaflet geometry, and anchoring is critical for fixation to the leaflet and heart wall.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein.

DETAILED DESCRIPTION

Figure 1:
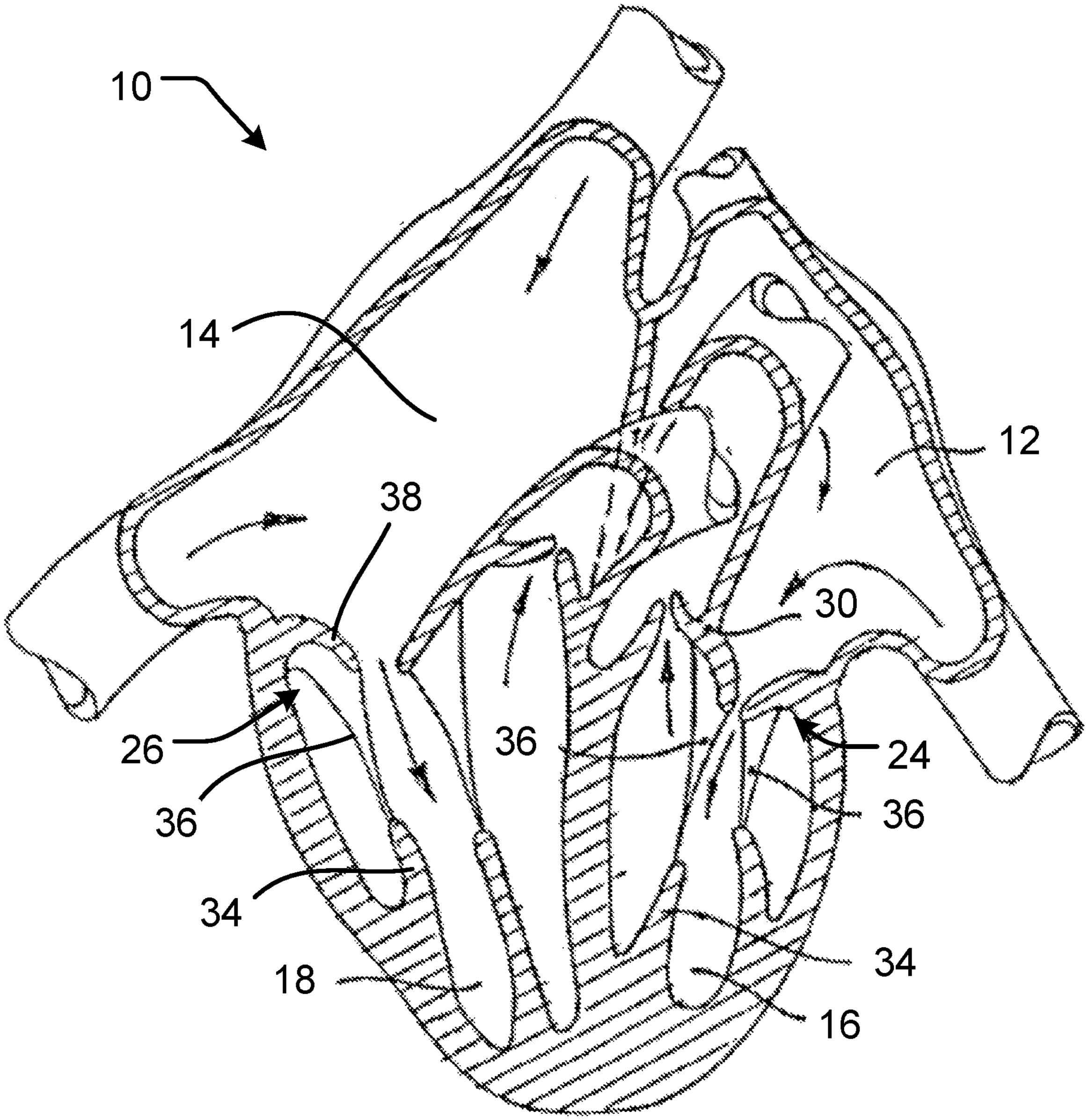
FIG. 1 is a cross-sectional view of a human heart.

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

The systems, apparatus and methods to repair operation of a heart valve of the present disclosure simplify repair of chordae tendineae, particularly by separating the anchoring of a replacement (artificial) chordae tendineae into multiple steps, mechanically and procedurally, while allowing for subsequent adjustability of the length of the replacement (artificial) chordae tendineae after anchoring, which correspondingly controls travel of the heat valve leaflet.

In certain embodiments an implant configured to control travel of a leaflet of a heart valve is provided, with the implant comprising a first implant member, the first implant member having a first implant member first fastener, a first implant member second fastener, a tether connecting the first implant member first fastener and the first implant member second fastener and a first implant member connector slidably disposed on the tether; a second implant member, the second implant member having a second implant member connector and a second implant member anchor; wherein the first implant member connector and the second implant member connector are magnetically couplable, and wherein at least one of the first implant member connector and the second implant member connector comprises a permanent magnet.

Referring now to FIG. 1, there is shown a human heart 10, which includes the left atrium 12 and the right atrium 14, and the left ventricle 16 and the right ventricle 18. The mitral valve 24, also known as the bicuspid valve or left atrioventricular valve, is between the left atrium 12 and left ventricle 16. The tricuspid valve 26, also known as the right atrioventricular valve, is similarly located between the right atrium 14 and right ventricle 18.

In a valve, such as the mitral valve 24, the mitral valve leaflets 30 are connected to the papillary stalk 34 by the chordae tendineae 36. Similarly, in the tricuspid valve 26, the tricuspid valve leaflets 38 are connected to the papillary stalk 34 by the chordae tendineae 36.

In certain instances, the native chordae tendineae 36, such as of the mitral valve 24 or the tricuspid valve 26, may tear, or otherwise function improperly between the mitral valve leaflets 30/tricuspid valve leaflets 38 and the papillary stalk 34, and need to be repaired with an implanted replacement artificial (i.e. replacement for native) chordae tendineae 36.

Figure 2:
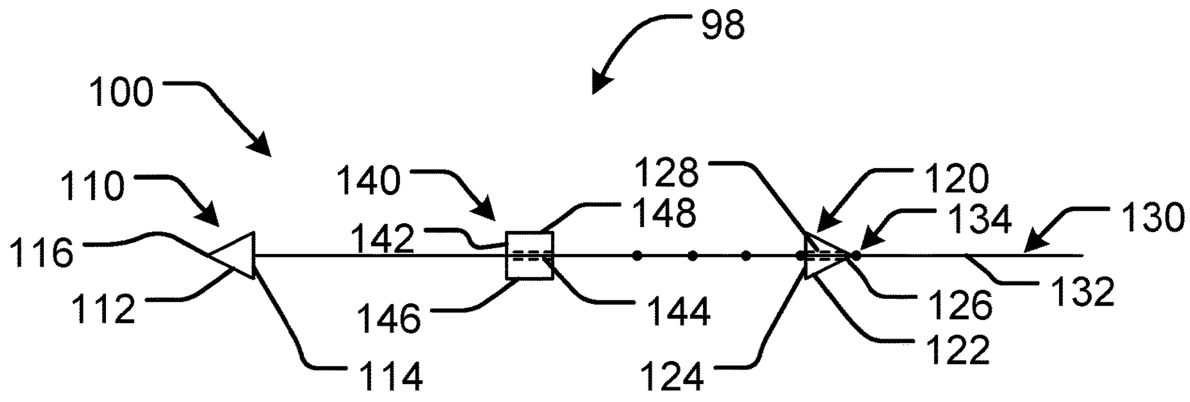
FIG. 2 is a side view of a first implant member of an implant according to the present disclosure.
Figure 3:
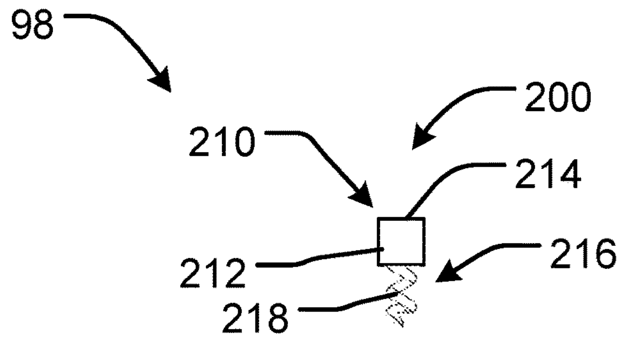
FIG. 3 is a side view of a second implant member of an implant according to the present disclosure.

Referring now to FIGS. 2-3, an implant 98 according to the disclosure comprises a first implant member 100 and a second implant member 200, which are configured to connect with one another to afford operation of the implant 98.

As shown, first implant member 100 comprises a first mechanical tissue fastener 110 and a second mechanical tissue fastener 120. First fastener 110 more particularly comprises a conical first fastener body 112 which narrows in diameter from a tissue retention (anchoring) end 114 to a tissue penetrating (pointed piercing) end 116.

Similar to first fastener 110, second fastener 120 comprises a conical second fastener body 122 which narrows in diameter from a tissue retention (anchoring) end 124 to a tissue penetrating (pointed piercing) end 126. In addition, second fastener body 122 also comprises a centrally located through hole (bore) 128 which extends from the tissue retention (anchoring) end 124 to the tissue penetrating (pointed piercing) end 126.

As such, first fastener 110 and second fastener 120 may be understood to be harpoon anchors.

First implant member 110 further comprises an elongated tether 130 which connects the first fastener 110 and the second fastener 120 and, more particularly, connects the first fastener body 112 and the second fastener body 122. Tether 130 comprises an elongated filament 132, which may have only one strand (i.e. mono-filament) or a plurality of strands (i.e. multi-filament) which may be, for example, fused, braided or otherwise bundled together. As shown, the elongated filament 132 extends through the through hole 128 of the second fastener body 122.

Filament 132 may be formed of a natural material (e.g. silk suture, gut suture, catgut suture) or synthetic material (e.g. synthetic polymer).

Tether 130 also comprises a plurality of locking elements 134 spaced from one another along the longitudinal length of the elongated filament 132. The position of the locking elements 134 is fixed on the elongated filament 132 such that the distance between the locking elements 134 relative to one another is also fixed. As explained below, the locking elements 134 adjustably fix the distance of the elongated filament 132 between the first fastener body 112 and the second fastener body 122. As shown, the locking elements 134 are also spaced from each other at a longitudinal length of the elongated filament 132 which is substantially equal (e.g. within 1 mm) to a longitudinal length of the second fastener body 122.

More particularly, the locking elements 134 have an outer diameter slightly larger than a diameter of the through hole 128 of the second fastener body 122, and hence interfere with free movement of the elongated filament 132 in the through hole 128 of the second fastener body 122 due to an interference fit. Stated another way, due to locking elements 134 having an outer diameter slightly larger than a diameter of the through hole 128 of the second fastener body 122, the locking element 134 adjacent the tissue penetrating end 126 of the second fastener body 122 will not freely enter the through hole 128 of the second fastener body 122. In such manner, the longitudinal length of the elongated filament 132 between the first fastener 110 and the second fastener 120 is inhibited from increasing.

Similarly, due to locking elements 134 having an outer diameter slightly larger than a diameter of the through hole 128 of the second fastener body 122 (e.g. 5-10% larger), the locking element 134 adjacent the tissue retention end 124 of the second fastener body 122 will not freely enter the through hole 128 of the second fastener body 122. In such manner, the longitudinal length of the elongated filament 132 between the first fastener 110 and the second fastener 120 is inhibited from decreasing.

Given that the longitudinal length of the elongated filament 132 between the first fastener 110 and the second fastener 120 is inhibited from both increasing and decreasing, the longitudinal length of the elongated filament 132 between the first fastener 110 and the second fastener 120 may be understood to be fixed.

However, the locking elements 134 may be made of a resiliently (elastically) deformable material (e.g. a polymer, particularly an elastomer) which allows them to elastically deform under a load directed to force (pull) the elongated filament 132 through the through hole 128 of the second fastener body 122.

In such case, the longitudinal length of the elongated filament 132 between the first fastener 110 and the second fastener 120 may be adjusted by the locking elements 134 traveling within the through hole 128 of the second fastener body 122. In the foregoing manner, a longitudinal length of the elongated filament 132 between the first fastener 110 and the second fastener 120 is adjustably fixable.

First implant member 110 further comprises a first implant member connector 140 which is configured to join with and separate from (i.e. releasably join), second implant member connector 210 of second implant member 200, as explained in greater detail below.

More particularly, first implant member connector 140 comprises a first implant member connector body 142 configured to releasably join with second implant member connector body 212 of second implant member connector 210.

As shown, first implant member connector body 142 comprises a through hole (bore) 144, through which filament 132 of tether 130 extends. The diameter of through hole 144 is great enough to enable first implant member connector body 142 to free slide along a length of filament 132, as well as the locking elements 134, without deforming them. As such the through hole 144 has a diameter slightly larger than the outer diameter of the locking elements 134 (e.g. 5-10% larger).

First implant member connector body 142 preferably comprises a magnet, and more particularly comprises a permanent magnet (e.g. a ferrite magnet). Even more particularly, first implant member connector body 142 preferably comprises a rare-earth magnet, such as a neodymium magnet and/or a samarium-cobalt magnet. As used herein, a rare-earth magnet may be prepared from at least one rare-earth element, such as cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), and yttrium (Y).

As such, the opposing sides 146 and 148 of first implant member connector body 142 may have opposite polarities, such as side 146 having a negative (−) polarity and side 148 having a positive (+) polarity.

Similarly, second implant member connector body 212 preferably comprises a magnet, and more particularly comprises a permanent magnet (e.g. a ferrite magnet). Even more particularly, second implant member connector body 212 preferably comprises a rare-earth magnet, such as a neodymium magnet and/or a samarium-cobalt magnet. As used herein, a rare-earth magnet may be prepared from at least one rare-earth element, such as cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), and yttrium (Y).

Side 214 of second implant member connector body 212 may have a positive (+) polarity or a negative (−) polarity.

On the opposite side of side 216 of second implant member connector body 212, second implant member 200 comprises a mechanical tissue anchor 218. As shown, anchor 218 comprises a mechanically engaged (threaded) anchor having a helical thread.

Figure 4:
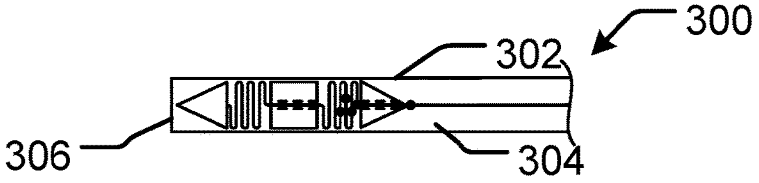
FIG. 4 is side view of the first implant member of an implant within a delivery catheter according to the present disclosure.

Referring now to FIG. 4, in certain embodiments, first implant member 100, as well as second implant member 200, may be delivered into the heart using an introducer/catheter 300. As shown first implant member 100 may be contained within the lumen 304 of the introducer/catheter body 302, in a manner such does not extend beyond the distal end 306 of the introducer/catheter body 302, until such is ready to be implanted.

Figure 5:
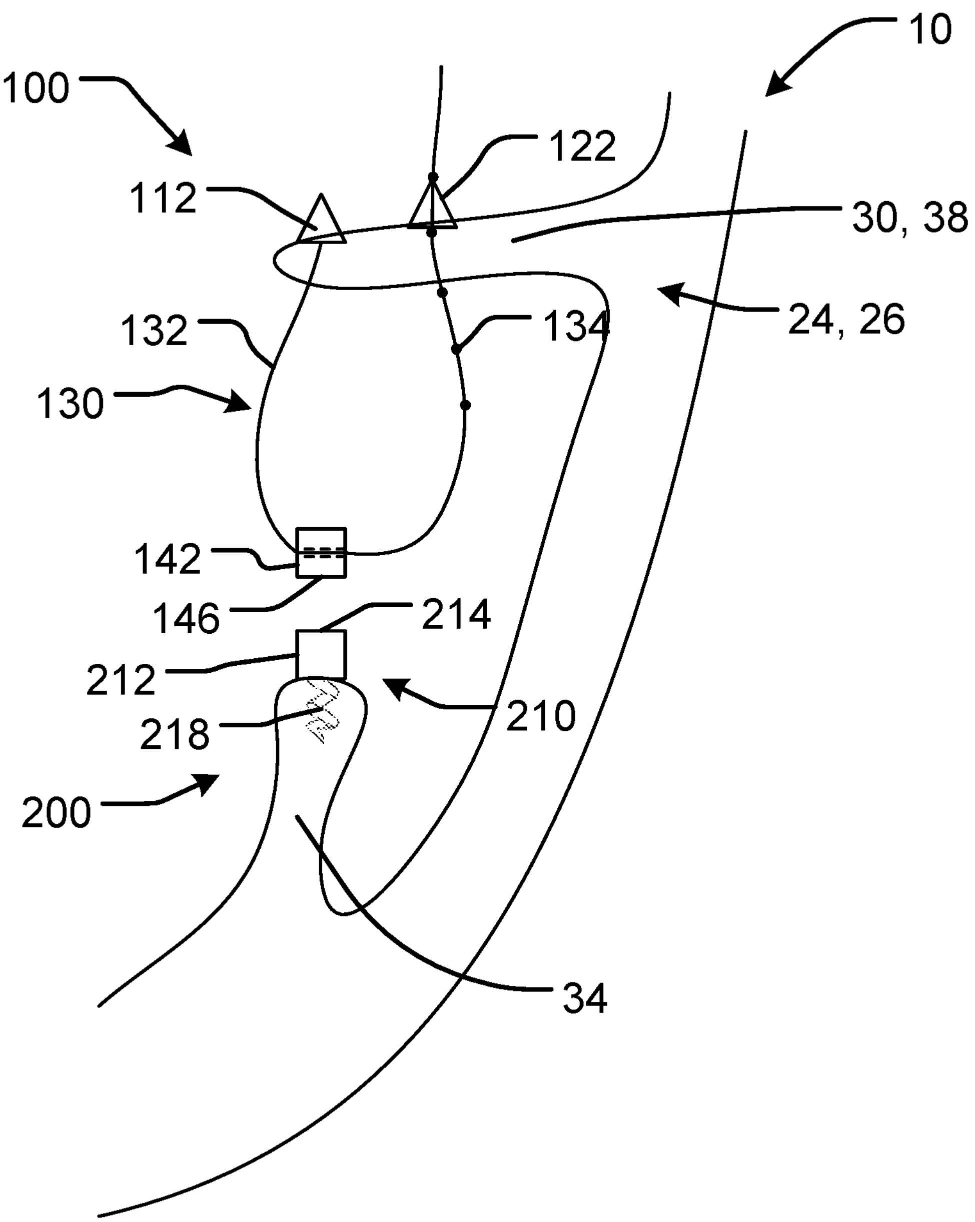
FIG. 5 is a first close-up view of the implant being installed in a heart.

Referring now to FIG. 5, during an implantation procedure, anchor 218 of second implant member 200 may be first anchored in the heart wall, particularly to papillary stalk 34 of the heart, which originate in the ventricular wall of the heart 10. The second implant member 200 may be implanted internally via a trans-septal approach of the introducer/catheter 300.

During implantation, the anchor 218 of second implant member 200 may be rotated such that the helical thread of anchor 218 engages and threads into the papillary stalk 34. As shown, when second implant member 200 is anchored to the heart 10, it is not connected to first implant member 100.

After second implant member 200 is implanted, the first fastener 110 of first implant member 100 may be deployed from the introducer/catheter 300 such that the first fastener body 112 pierces a hole in leaflet 30 (or 38) of mitral valve 24 (or tricuspid valve 26) and extends through the hole. As shown the first fastener 110 is deployed such that the first fastener body 112 resides on the side of the leaflet 30 which faces the atrium 12 (or atrium 14), with the tissue retention end 114 of the first fastener body 112 disposed on the side of the leaflet 30 which faces the atrium 12 (or atrium 14). Alternatively, the leaflet 30 (or 38) of mitral valve 24 (or tricuspid valve 26) may be pierced with a separate needle or wire passed through the introducer/catheter 300.

The first implant member 100 may then be further deployed such that tether 130 is unfolded, and first implant member connector 140 and second fastener 120 are removed from the introducer/catheter 300.

As shown, the second fastener 120 of first implant member 100 may be deployed from the introducer/catheter 300 such that the second fastener body 122 pierces a second hole in the leaflet 30 (or 38) of mitral valve 24 (or tricuspid valve 26) and extends through the hole. As shown the second fastener 120 is deployed such that the second fastener body 122 resides on the side of the leaflet 30 which faces the atrium 12 (or atrium 14), with the tissue retention end 124 of the second fastener body 122 disposed on the side of the leaflet 30 which faces the atrium 12 (or atrium 14). Alternatively, the leaflet 30 (or 38) of mitral valve 24 (or tricuspid valve 26) may be pierced with a separate needle or wire passed through the introducer/catheter 300.

As shown, in FIG. 5, the first fastener 110 and second fastener 120 of the first implant member 100, and the anchor 218 of the second implant member 200, are fastened (anchored) in the leaflet 30 (or 38) and to the papillary stalk 34, respectively, prior to any connection of the first implant member 100 and second implant member 200 to one another.

Figure 6:
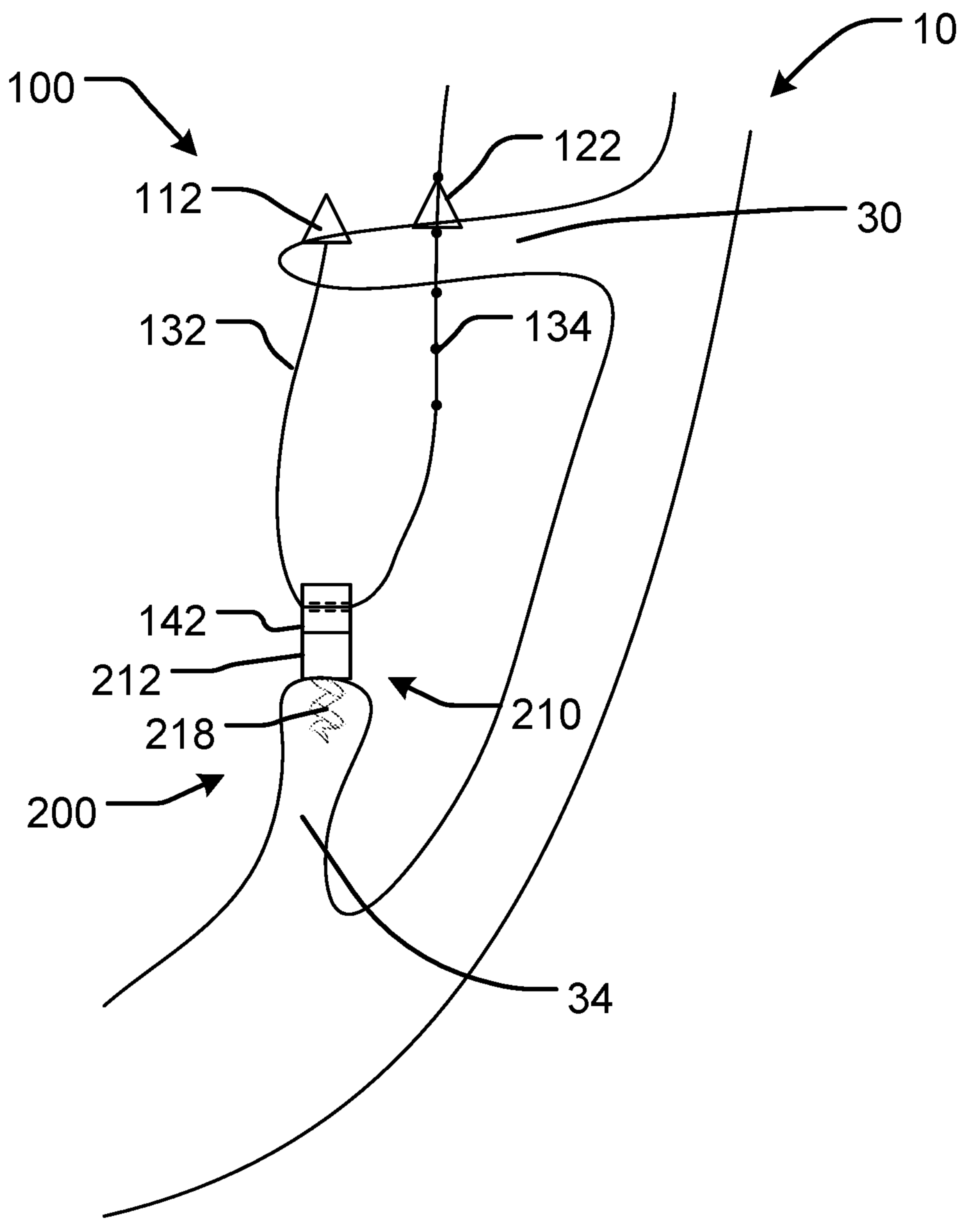
FIG. 6 is a second close-up view of the implant being installed in a heart.

Referring now to FIG. 6, the first implant member connector 140 and second implant member connector 210 may then be coupled together. More particularly, the first implant member connector body 142 and second implant member connector body 212 may be magnetically coupled together, by virtue of one or both of the first implant member connector body 142 and the second implant member connector body 212 comprising a magnet, particularly a permanent magnet and more particularly a rare-earth permanent magnet.

If only one of the first implant member connector body 142 and the second implant member connector body 212 comprises the magnet, then the other connector body 142 or 212 may comprise a magnetic material, and more particularly a ferromagnetic material, which will couple magnetically with the magnet of the other connector body 142 or 212. Exemplary magnetic materials include cobalt, hematite, iron, nickel, carbon steel and certain stainless steels, which include iron and have a crystal structure be arranged in a ferritic or a martensitic structure. Magnetic stainless steel may include ferritic stainless steel (e.g. grades 409, 430 and 439), martensitic stainless steel (e.g. grades 410, 420 and 440) or duplex stainless steel which contains a mixture of austenite and ferrite (e.g. grade 2205).

If both the first implant member connector body 142 and the second implant member connector body 212 comprises the magnet, then side 146 of first implant member connector body 142 and side 214 of second implant member connector body 212 may each provide a magnet which have opposite polarities (positive (+) and negative (−)) as to be magnetically attracted to one another when within a certain distance of one another. As shown in FIG. 5, after the first fastener 110 and second fastener 120 of the first implant member 100, and the anchor 218 of the second implant member 200, are anchored in the leaflet 30 (or 38) and to the papillary stalk 34, respectively, but prior to the first implant member connector body 142 and the second implant member connector body 212 making physical contact with one another, the filament 132 of the tether 130 has a longitudinal length disposed between the first fastener 110 and the second fastener 120 which is long enough to permit the leaflet 30 (or 38) to operate (i.e. open and close) unconstrained by the tether 130.

Referring now to FIG. 6, in contrast to FIG. 5, the first implant member connector body 142 and the second implant member connector body 212 are now in physical contact with one another and magnetically coupled. As shown, while the filament 132 of the tether 130 is more taut than on FIG. 5, the filament 132 of the tether 130 has a longitudinal length disposed between the first fastener 110 and the second fastener 120 which is long enough to permit the leaflet 30 (or 38) to operate unconstrained by the tether 130.

Figure 7:
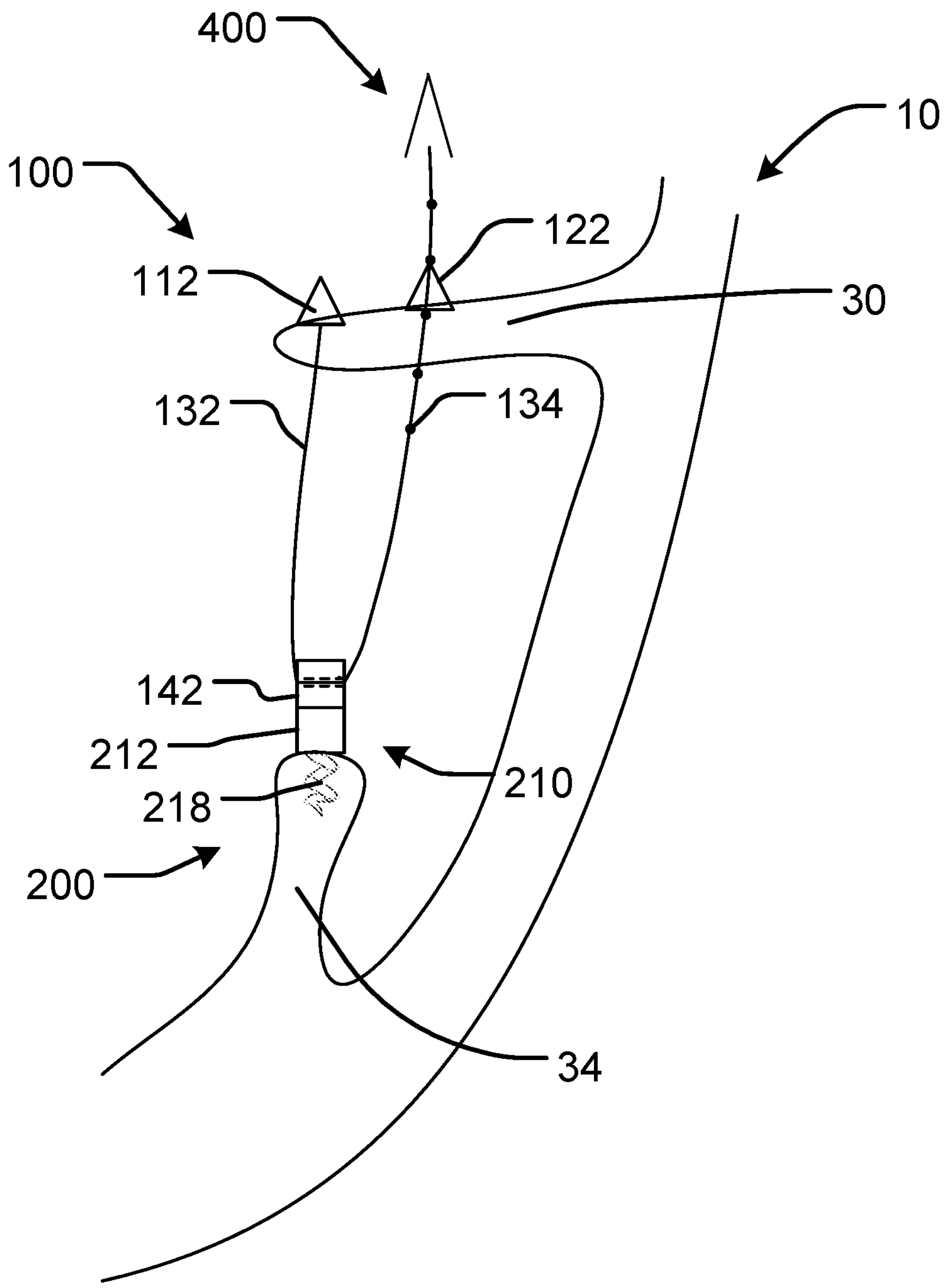
FIG. 7 is a third close-up view of the implant being installed in a heart.

Referring to FIG. 7, once the first implant member connector body 142 and the second implant member connector body 212 are in physical contact with one another, the longitudinal length of the filament 132 of the tether 130 disposed between the first fastener 110 and the second fastener 120 may be adjusted, by being decreased, as to constrain opening and closing movement of the leaflet 30 (or 38).

More particularly, the filament 132 of the tether 130 may be pulled through the through hole 128 of the second fastener body 122, particularly adjacent the tissue penetrating end 124 of the second fastener body 122, such as by a grasping device 400 (e.g. forceps), to shorten, and thereby adjust, the longitudinal length of the filament 132 of the tether 130 disposed between the first fastener 110 and the second fastener 120. In the foregoing manner, the opening and closing movement (travel) of the leaflet 30 (or 38) may be decreased, as compared to prior to the implantation of the implant 98, particularly by being inhibited by the length of the filament 132 of the tether 130 disposed between the first fastener 110 and the second fastener 120.

As set forth above, tether 130 comprises a plurality of deformable locking elements 134 spaced from one another along the longitudinal length of the elongated filament 132. The deformable locking elements 134 adjustably fix the distance of the elongated filament 132 between the first fastener body 112 and the second fastener body 122.

As such, when the filament 132 of the tether 130 is pulled through the through hole 128 of the second fastener body 122 by a grasping device 400, the longitudinally directed pulling force applied to the filament 132 via the grasping device 400 is significant enough to overcome the bias of the resilience of the locking elements 134, in which case the locking element 134 adjacent the tissue retention end 124 of the second fastener body 122 deforms, which causes the locking element 134 to enter and travel within through hole 128 towards the tissue penetrating end 126 of the second fastener body 122, thus shortening, the longitudinal length of the filament 132 of the tether 130 disposed between the first fastener 110 and the second fastener 120. When the filament 132 of the tether 130 is pulled through the through hole 128 of the second fastener body 122 such that the locking element 134 within the through hole 128 exits the through hole 128 adjacent the tissue penetrating end 126 of the second fastener body 122, the resilience (elasticity) of the locking element 134 may enable the locking element 134 to regain its undeformed state, and the longitudinal length of the filament 132 of the tether 130 disposed between the first fastener 110 and the second fastener 120 may be fixed in position once again.

For perhaps more fine tuning of the length of movement (travel) of the opening and closing movement of the leaflet 30 (or 38) with the implant 10 of the present disclosure, the travel length of the leaflet 30 (or 38) may also be adjusted by rotation of the second implant member connector body 212 (e.g. via forceps) of second implant member 200, either further out of, or further into, the papillary stalk 34 while the first implant member connector body 142 is inhibited by rotating (e.g. via forceps). As such, the second implant member 200 may be adjustable axially by adjustable fixation depth. Thus, the implant 10 of the present disclosure provides multiple means to adjust the length of movement (travel) of the opening and closing movement of the leaflet 30 (or 38) with the implant 10.

Alternatively, the second fastener 120 of first implant member 100 may be anchored to the leaflet 30 (or 38) of mitral valve 24 (or tricuspid valve 26) after the first implant member connector 140 and second implant member connector 210 are magnetically coupled.

Figure 8:
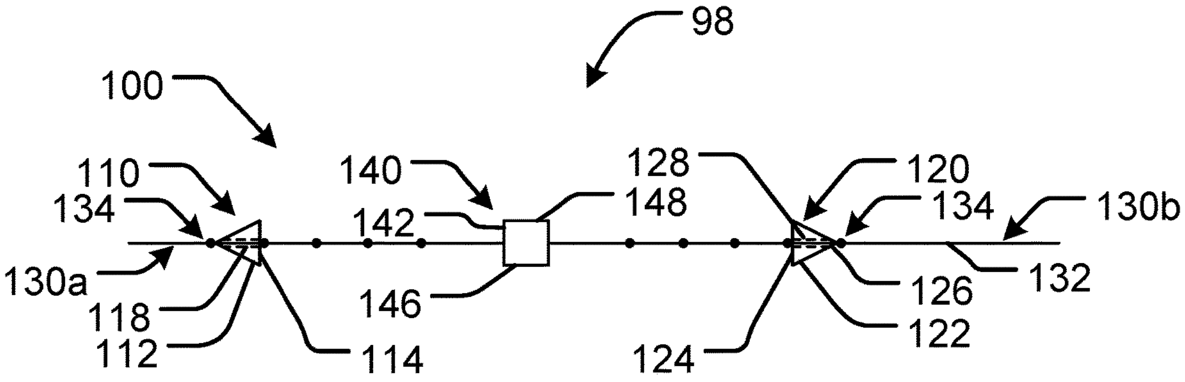
FIG. 8 is a side view of another embodiment of a first implant member of an implant according to the present disclosure.

FIG. 8 depicts another illustrative implant 98 according to the disclosure. The illustrative implant 98 includes a first implant member 100 configured to connect with a second implant member 200 (not depicted in FIG. 8) to afford operation of the implant 98.

Similar to the implant 98 depicted in FIG. 2, the implant 98 depicted in FIG. 8 includes a conical-shaped first mechanical tissue fastener 110 and a conical-shaped second mechanical tissue fastener 120. In embodiments, both the first mechanical tissue fastener 110 and second mechanical tissue fastener 120 may each be understood to include harpoon anchors.

In contrast to the implant 98 depicted in FIG. 2, the implant 98 depicted in FIG. 8 includes an elongated tether 130 having a first portion 130*a* that passes through an through-hole 118 formed in the first mechanical tissue fastener 110 and a second portion 130*b* that passes through an through-hole 128 formed in the second mechanical tissue fastener 120. Tether 130 includes an elongated filament 132, which may have only one strand (i.e. mono-filament) or a plurality of strands (i.e. multi-filament) which may be, for example, fused, braided or otherwise bundled together. Filament 132 may be formed of a natural material (e.g. silk suture, gut suture, catgut suture) or synthetic material (e.g. synthetic polymer).

The first portion 130*a* of the elongated filament 132 and the second portion 130*b* of the elongated filament 132 each include a plurality of locking elements 134 spaced apart from one another along the longitudinal length of the first portion 130*a* of the elongated filament 132 and the second portion 130*b* of the elongated filament 132, respectively. The position of the locking elements 134 along both the first portion 130*a* and the second portion 130*b* of the elongated filament 132 is fixed on the elongated filament 132 such that the distance between the locking elements 134 relative to one another is also fixed. Similar to the implant 98 depicted in FIG. 2, the locking elements 134 adjustably fix the distance of the elongated filament 132 between the first fastener body 112 and the second fastener body 122. As shown, the locking elements 134 are also spaced from each other at a longitudinal length of the elongated filament 132 which is substantially equal (e.g. within 1 mm) to a longitudinal length of the second fastener body 122.

More particularly, the locking elements 134 have an outer diameter slightly larger than a diameter of the through-hole 118 in the first mechanical tissue fastener 110 and a diameter of the through-hole 128 in the second mechanical fastener 120. The locking elements 134 thus interfere with free passage of the first portion 130*a* of the elongated filament 132 through the through-hole 118 in the first mechanical tissue fastener 110 and interfere with free passage of the second portion 130*b* of the elongated filament 132 through the through-hole 128 in the second mechanical tissue fastener 120. In such manner, the longitudinal length of the elongated filament 132 between the first fastener 110 and the second fastener 120 is inhibited from increasing.

Similarly, due to locking elements 134 having an outer diameter slightly larger than a diameter of the through-hole 118 in the first mechanical tissue fastener 110 and a diameter of the through-hole 128 in the second mechanical fastener 120, the locking elements 134 prevent the longitudinal length of the elongated filament 132 between the first fastener 110 and the second fastener 120 from decreasing. Given that the longitudinal length of the elongated filament 132 between the first fastener 110 and the second fastener 120 is inhibited from both increasing and decreasing, the longitudinal length of the elongated filament 132 between the first fastener 110 and the second fastener 120 may be understood to be fixed.

In embodiments, the locking elements 134 may include a resiliently (elastically) deformable material (e.g. a polymer, particularly an elastomer) that permits an elastic deformation elastically deform under a load directed to force (pull) the first portion 130*a* of the elongated filament 132 through the through-hole 118 in the first mechanical tissue fastener 110 and/or the second portion 130*b* of the elongated filament 132 through the through-hole 128 in the second mechanical tissue fastener 120. In such embodiments, the longitudinal length of the elongated filament 132 between the first mechanical tissue fastener 110 and the second mechanical tissue fastener 120 may be adjusted by the locking elements 134 traveling within the through hole 128 of the second fastener body 122. In the foregoing manner, a longitudinal length of the elongated filament 132 between the first mechanical tissue fastener 110 and the second mechanical tissue fastener 120 is adjustably fixable.

Figure 9:
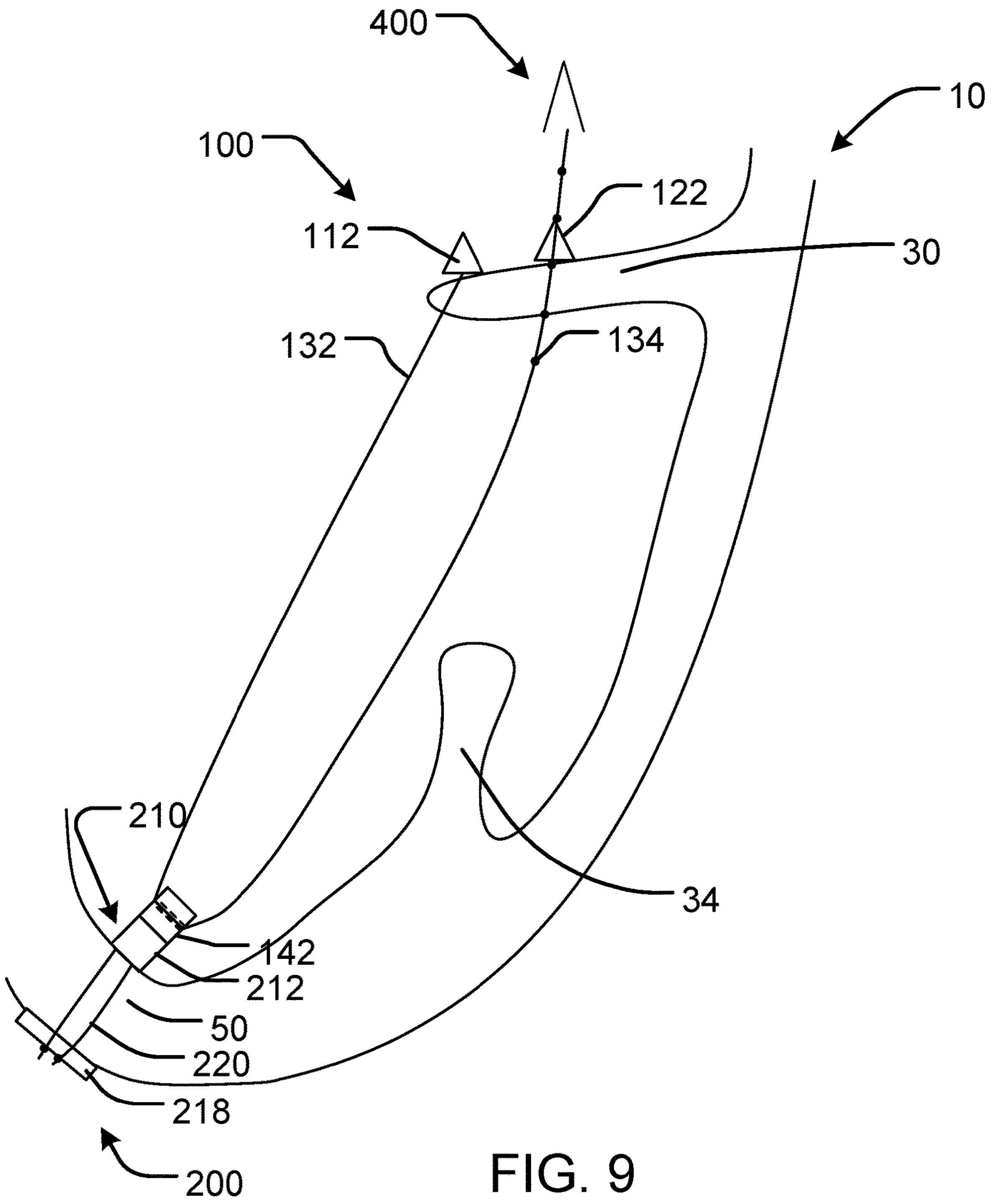
FIG. 9 is a side view of another embodiment of a second implant member of an implant according to the present disclosure.

In another embodiment, as shown in FIG. 9, the second implant member 200 may be anchored in the heart wall at the left ventricular apex 50 located at the bottom of the left ventricle 16 inferior to both the mitral valve 24 and aortic valve, particularly as part of an external (trans-apical) approach. Similar to the prior embodiments, second implant member 200 may be implanted before the first implant member 100. The second implant member 200 may also comprise a tether 220, similar to tether 130, which couples between the second implant member connector body 212 and the anchor 218. In such instance, the tether 220 may extend through the wall of the heart, and be attached to an anchor 218 which is disposed adjacent an outer side of the heart. The anchor 218 may comprise a pledget (e.g. expanded PTFE pledget) or similar button (planar disc or circular plate) anchoring device to secure the tether 220.

Figure 10:
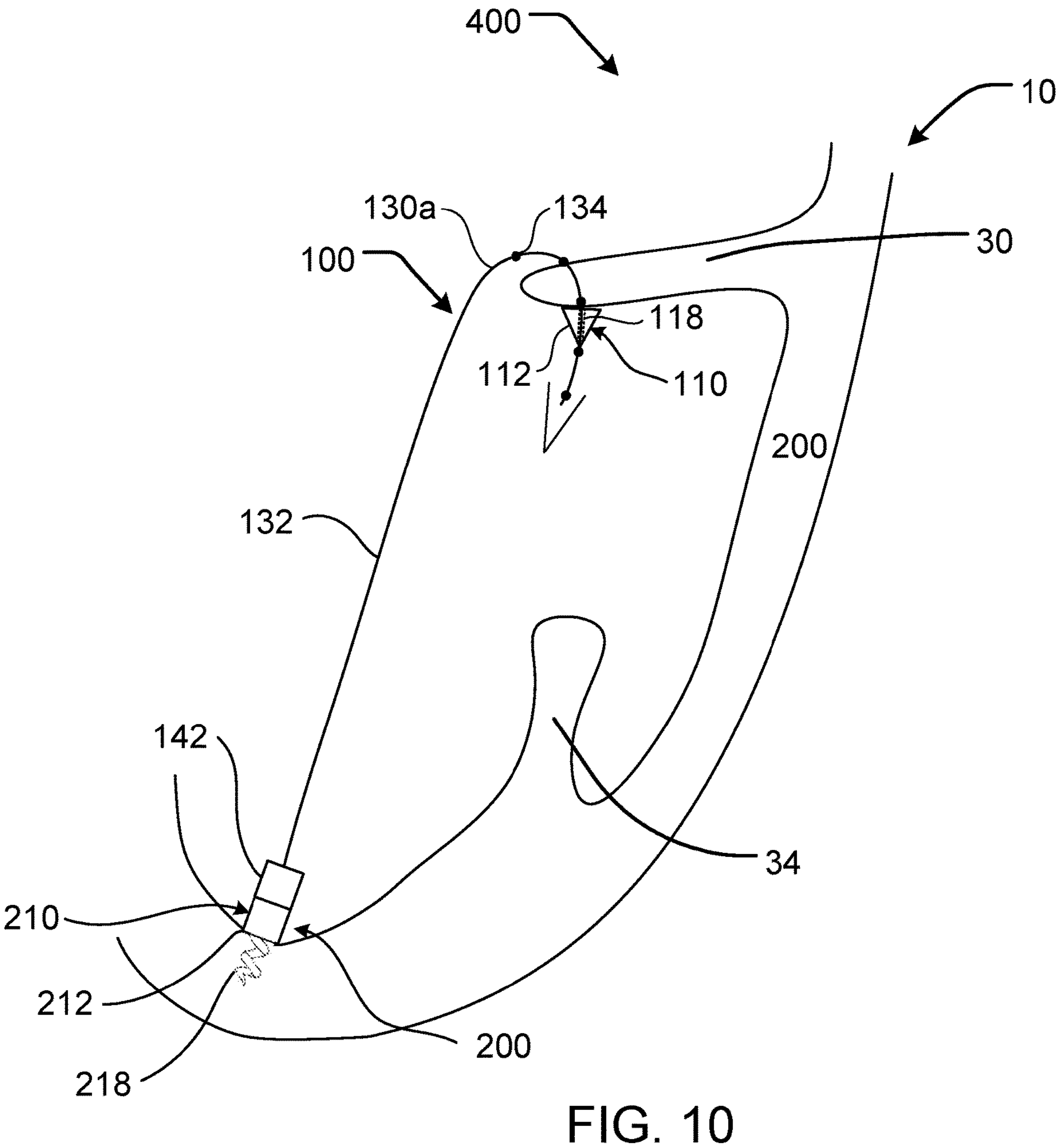
FIG. 10 is a side view of another embodiment of an implant according to the present disclosure.

FIG. 10 depicts yet another illustrative embodiment in which the second implant member 200 may be anchored in the heart wall at the left ventricular apex 50 located at the bottom of the left ventricle 16 inferior to both the mitral valve 24 and aortic valve, particularly as part of an external (trans-apical) approach. As depicted in FIG. 10, in such embodiments, the first implant member 100 may include only a single first mechanical tissue fastener 110 coupled to the first implant member connector body 142 via only the first portion 130*a* of the elongated filament 132. In such embodiments, the elongated filament 132 may pass over the mitral valve leaflet 30 and the first mechanical tissue fastener 110 may penetrate the mitral valve leaflet 30 from top to bottom. Such an arrangement beneficially permits placement of the second implant member 200 in the heart wall and the penetration of the mitral valve leaflet 30 from above, simplifying the implantation of both the first implant member 100 and the second implant member 200. The length of the elongated filament 132 may be adjusted by passing the locking elements 134 through the through-hole 118 in the first mechanical tissue fastener 110 to achieve a desired length of the elongated filament 132.

Figure 11:
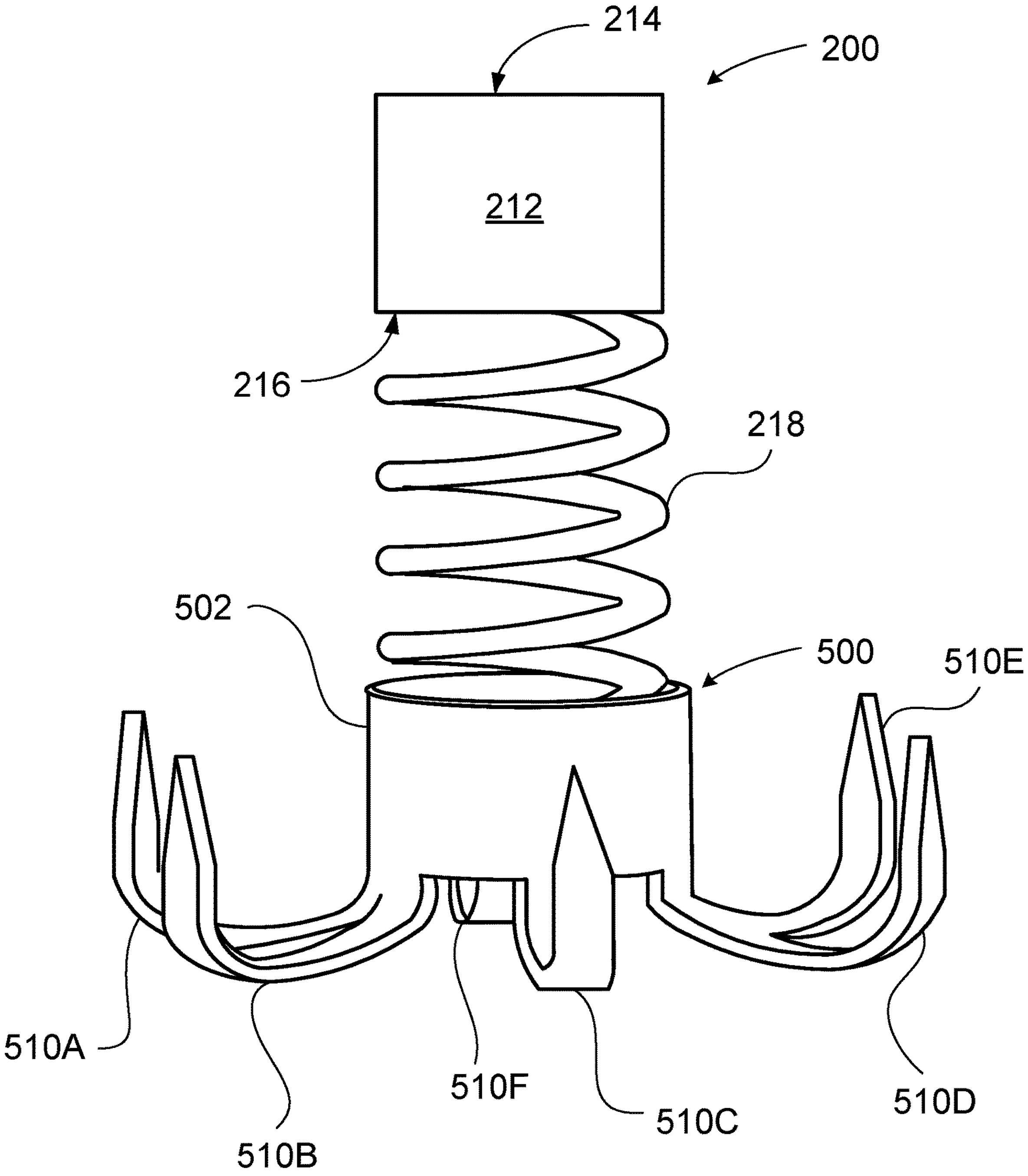
FIG. 11 is a side view of another second implant member of an implant according to the present disclosure.

FIG. 11 depicts another illustrative second implant member 200 that includes a shape memory alloy anchor 500 that includes a central receiver portion 502 to receive the tissue anchor 218 portion of the second implant member 200 and additionally includes a plurality of shape memory alloy hook members 510A-510*n* (collectively "shape memory alloy hook members 510," six such shape memory alloy hook members 510A-510F are depicted in FIG. 11).

As depicted in FIG. 11, the second implant member 200 may be deployed using a catheter—in such a deployment, the shape memory alloy hook members 510 extend longitudinally from the central receiver portion 502. Upon exiting the catheter, the shape memory alloy hook members 510 curve upward to assume the "fishhook" or "grappling hook" configuration depicted in FIG. 11. The curvature of the shape memory alloy hook members 510 into the fishhook configuration beneficially compresses the heart wall tissue surrounding the central receiver portion 502, thereby improving the performance of the tissue anchor 218. In addition, the shape memory alloy hook members 510 also spread the tensile forces placed on the second implant member by the elongated filament 132 across a larger heart wall area reducing the point tensile forces exerted on the heart wall.

In embodiments, the shape metal alloy anchor 500 may include one or more biologically compatible shape metal alloys, such as a Nickel-Titanium (NiTi) alloy. One of skill in the relevant arts will readily appreciate that a large number of biologically compatible shape metal alloys exist and other such alloys may be substituted with equal performance and efficiency.

From the foregoing disclosure, it should be understood that the present disclosure provides systems, apparatus and methods to repair operation of a heart valve, particularly by chordae tendineae repair and replacement, with the filament 132 of the tether 130 acting as a replacement (artificial) chordae tendineae. Further, after a period of implantation, the filament 132 may be coated with endothelial cells, which may result in a native replacement chordae tendineae, with the filament 132 providing a scaffold for the endothelial cells to proliferate.

Thus, the present disclosure discloses multiple, initially separate, implant members 100 and 200, with one implant member 100 having at least one fastener 110, 120 fastenable (anchorable) to a leaflet 30/38 of a valve 24/26, and another implant member 200 having at least one anchor 218 anchorable to the heart wall, such as the papillary stalk 34, and/or other wall of the heart tissue. Each implant member 100, 200 includes a connector 140, 210 which are configured to couple with each other via magnetic force. One of the implant members 100 further comprises a tether 130 which provides a replacement (artificial) chordae tendineae having a length with his adjustable after the connectors 140, 210 of the implant members 100, 200 are magnetically coupled.

It should be understood that, while a single continuous tether 130 is shown as extending from first fastener body 112 to second fastener body 122, particularly through through-hole 144 in the first implant member connector body 142, a plurality of continuous tethers 130 may extend continuously from the first fastener body 112 to the second fastener body 122 through through-hole 144. In such manner, if one of the tethers 130 should break, the first fastener 110 to second fastener 120 will still remain fastened together by another tether 130. Only one tether 130 is shown for the sake of clarity, and additional tethers 130 (e.g. 2, 3, 4, 5, 6, 7, 8, 9, 10) are not shown as merely being duplicative 9.

In another embodiment of first implant member 100, through hole 144 of the first implant member connector body 142 may be eliminated, and a first tether 130*a* may connect between the first fastener body 112 and the first implant member connector body 142, and a second tether 130*b* may connect between the second fastener body 122 and the first implant member connector body 142. Additionally, first fastener body 112 may include a centrally located through hole (bore) 118 which extends from the tissue retention (anchoring) end 114 to the tissue penetrating (pointed piercing) end 116, similar to that of second fastener body 122, as well as locking elements 134.

In the foregoing manner, each of the tethers 130*a*, 130*b* may have locking elements 134 to independently adjustably fix the distance of the first tether 130*a* between the first fastener body 112 and the first implant member connector body 142, and the second tether 130*b* between the second fastener body 122 and the first implant member connector body 142. It should be again understood that, while only one of each of tethers 130*a*, 130*b* is shown, additional tethers 130*a*, 130*b* (e.g. 2, 3, 4, 5, 6, 7, 8, 9, 10) are contemplated, but are not shown for the sake of clarity, as merely being duplicative.

While a preferred embodiment of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

LISTING OF REFERENCE CHARACTERS

10 heart
12 left atrium
14 right atrium

16 left ventricle
18 right ventricle
24 mitral (bicuspid) valve
26 tricuspid valve
30 mitral valve leaflets
34 papillary stalk
36 chordae tendineae
38 tricuspid valve leaflets
50 apex of the heart
98 implant
100 first implant member
110 first fastener
112 first fastener body
114 tissue retention (anchoring) end
116 tissue penetrating (pointed piercing) end
118 through-hole
120 second fastener
122 second fastener body
124 tissue retention (anchoring) end
126 tissue penetrating (pointed piercing) end
128 through-hole
130 tether
132 filament
134 locking elements
140 first implant member connector
142 first implant member connector body
144 through hole
146 side of first implant member connector body
148 side of first implant member connector body
200 second implant member
210 second implant member connector
212 second implant member connector body
214 side of second implant member connector body
218 anchor
220 tether
300 introducer/catheter
302 introducer/catheter body
304 lumen
306 distal end
400 grasping device
500 shape memory alloy anchor
502 central receiver portion
510 shape memory alloy hook member

What is claimed is:

1. An implant configured to control travel of a leaflet of a heart valve, the implant comprising:
a first implant member that includes:
a first mechanical tissue fastener;
a second mechanical tissue fastener;
a first implant member connector; and
an adjustable length tether connecting the first mechanical tissue fastener disposed at a first end portion of the tether and the second mechanical tissue fastener disposed along a second end portion of the tether, and the first implant member connector; and
a second implant member that includes:
a magnetic second implant member connector; and
a tissue anchor;
wherein the first implant member connector and the second implant member connector are magnetically couplable; and
wherein the second mechanical tissue fastener slideably displaceable along the second portion of the adjustable length tether; wherein the second portion of the adjustable length tether includes a plurality of fixed, spaced-apart, locking elements to maintain the second mechanical tissue fastener at a fixed location on the second portion of the adjustable length tether; wherein the first implant member connector further includes an through-hole to accommodate passage of the adjustable length tether through the second implant member connector, such that the first implant member connector is disposed at a location along the adjustable length tether between the first mechanical tissue fastener and the a second mechanical tissue fastener.

2. The implant of claim 1 wherein the locking elements include elastically deformable locking elements, the elastically deformable locking elements to deform to pass through the through-hole.

3. The implant of claim 1 wherein the first implant member connector includes a magnetic first implant member connector.

4. The implant of claim 1 wherein the first implant member connector includes one or more magnetic materials.

5. The implant of claim 1 wherein the magnetic second implant member connector includes a rare earth magnetic material.

6. The implant of claim 1 wherein the second implant member further includes a shape memory alloy anchor.

7. The implant of claim 6 wherein the shape memory alloy anchor includes a central receiver portion to receive the tissue anchor and a plurality of shape memory alloy hook members.

8. The implant of claim 1 wherein the tissue anchor comprises a helical tissue anchor.

* * * * *